US009486378B2

(12) United States Patent
Bohnen et al.

(10) Patent No.: US 9,486,378 B2
(45) Date of Patent: Nov. 8, 2016

(54) HEAT THERAPY DEVICE

(71) Applicant: Dräger Medical GmbH, Lübeck (DE)

(72) Inventors: Thomas Bohnen, Lübeck (DE); Tjeerd Jan Pieter Gerbranda, GJ Den Haag (NL); Markus Hampe, Lübeck (DE); Jochim Koch, Ratzeburg (DE); Philip Möhring, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 174 days.

(21) Appl. No.: 14/388,465

(22) PCT Filed: Mar. 20, 2013

(86) PCT No.: PCT/EP2013/055845
§ 371 (c)(1),
(2) Date: Sep. 26, 2014

(87) PCT Pub. No.: WO2013/143949
PCT Pub. Date: Oct. 3, 2013

(65) Prior Publication Data
US 2015/0065787 A1 Mar. 5, 2015

(30) Foreign Application Priority Data
Mar. 27, 2012 (DE) .................. 10 2012 006 204

(51) Int. Cl.
*A61G 11/00* (2006.01)
*A61N 5/06* (2006.01)
(52) U.S. Cl.
CPC ............. *A61G 11/005* (2013.01); *A61G 11/00* (2013.01); *A61G 11/006* (2013.01); *A61N 5/0625* (2013.01); *A61G 11/002* (2013.01); *A61G 2203/30* (2013.01); *A61N 2005/0659* (2013.01)

(58) Field of Classification Search
CPC .. A61G 11/00; A61G 11/002; A61G 11/005; A61G 11/006; A61G 2203/30; A61G 11/008; A61G 11/009; A61G 7/005–7/018; A61N 2005/0659; A61N 5/0625; A61N 5/0614; F16M 11/04; A61F 7/00
USPC ...................................... 248/125.2
See application file for complete search history.

(56) References Cited

U.S. PATENT DOCUMENTS 3,782,362 A * 1/1974 Puzio .................. A61G 11/00
128/205.26
4,312,331 A 1/1982 Hahmann
(Continued)

FOREIGN PATENT DOCUMENTS

DE 29 13 282 A1 10/1980
DE 31 12 300 A1 10/1982
(Continued)

Primary Examiner — John Lacyk
(74) Attorney, Agent, or Firm — McGlew and Tuttle, P.C.

(57) ABSTRACT

A heat therapy device, in particular an incubator, for treating newborn children, has a bordered lying surface (4) freely accessible from above for accommodating a newborn child. A hood (18) can be moved between a closed position in which the bordered lying surface (4) is covered and an open exposed bordered lying surface position. A radiation heater (16) is suspended from a support structure (8) and is directed at the surface (4), in such a way that, after the movement from the closed position to the open position, the end (18b) of the hood facing the support structure (8) lies vertically at least at the height of the radiation heater (16) and lies horizontally further from the support structure (8) than the radiation heater, such that the hood (18) assumes a position outside of a radiation cone (16a) from the radiation heater (16) onto the lying surface (4).

23 Claims, 6 Drawing Sheets

(56) References Cited

U.S. PATENT DOCUMENTS

| | | | |
|---|---|---|---|
| 5,971,914 A | 10/1999 | Donnelly et al. | |
| 6,231,499 B1 | 5/2001 | Jones | |
| 6,893,390 B1 * | 5/2005 | Mackin | A61G 11/00 5/603 |
| 7,282,022 B2 | 10/2007 | Falk et al. | |
| 2002/0143233 A1 * | 10/2002 | Donnelly | A61F 7/00 600/22 |
| 2003/0045773 A1 * | 3/2003 | Costanzo | A61G 11/00 600/22 |
| 2007/0001076 A1 * | 1/2007 | Asamarai | F16M 11/04 248/281.11 |
| 2008/0283691 A1 * | 11/2008 | Bliven | F16M 11/10 248/125.2 |
| 2010/0076248 A1 * | 3/2010 | Ibara | A61G 11/00 600/22 |
| 2010/0127144 A1 * | 5/2010 | Lange | F16M 11/04 248/284.1 |
| 2010/0286471 A1 * | 11/2010 | Matsubara | A61G 11/00 600/22 |

FOREIGN PATENT DOCUMENTS

| | | |
|---|---|---|
| DE | 20 2005 021 580 U1 | 11/2008 |
| DE | 10 2010 014561 A1 | 11/2010 |
| EP | 2 168 545 A1 | 3/2010 |
| EP | 2 179 718 A2 | 4/2010 |
| WO | 2009/073693 A1 | 6/2009 |

* cited by examiner

HEAT THERAPY DEVICE

CROSS REFERENCE TO RELATED APPLICATIONS

This application is a United States National Phase application of International Application PCT/EP2013/055845 filed Mar. 20, 2013 and claims the benefit of priority under 35 U.S.C. §119 of German Patent Application DE 10 2012 006 204.4 filed Mar. 27, 2012, the entire contents of which are incorporated herein by reference.

FIELD OF THE INVENTION

The present invention pertains to a thermotherapy device, especially an incubator, for the treatment of newborns with a bordered reclining surface which is freely accessible from above for receiving a newborn, with a hood that is movable between a closed position covering the reclining surface and an open position exposing the reclining surface, and with a radiant heater suspended from a support structure, directed toward the reclining surface.

BACKGROUND OF THE INVENTION

Such a thermotherapy device is known, for example, from DE 20 2005 021 580 U1. The prior-art thermotherapy device has a hood which is vertically movably suspended from a support structure. Further, a radiant heater, which is directed toward the reclining surface, is mounted on the support structure. In the open position of the hood, this hood still lies vertically below the radiant heater. The hood is partly transparent for IR radiation, such that heat radiation directed toward the reclining surface by the radiant heater can irradiate IR-transparent parts of the hood and can thus reach the reclining surface. A continuous feed of heat can be achieved with this device, i.e., the radiant heater can operate without interruption, while the hood is moved from the closed position into the open position or vice versa. However, the heat radiation from the radiant heater is nevertheless weakened when passing through the partly IR-transparent hood. The material for the IR-transparent areas is very expensive, on the one hand, and the IR-transparent areas can only be integrated into the hood with difficulty, on the other hand.

Another thermotherapy device is known from U.S. Pat. No. 6,231,499 B1. Here, the hood is moved upwards via an electric linear drive, as a result of which the opening process has a relatively long duration. The radiant heater is integrated within the hood. For safety reasons, it only switches on when the hood is moved fully up, and must be immediately switched off again when moving the hood down and must be covered by means of a hinged cover in order to protect the baby from the radiator which is still very hot at this point in time. A simultaneous heating of the hood in the closed state, for example, for avoiding condensation from steam on the inner wall of the hood and for avoiding radiation losses of the baby, is not possible.

A thermotherapy device with fixed heating radiator and with a flap in the hood, which must be open in order to be able to radiate the child unhindered with the hood being open, is known from U.S. Pat. No. 7,282,022. This requires complicated mechanics. In addition, the full heat radiation reaches the infant only with the hood raised up and with the flap being open.

Another thermotherapy device is known from U.S. Pat. No. 5,971,914 B1. Here, two hood parts, separated in length, are carried by the radiant heater, whereby both hood parts are folded upwards when opening. The radiant heater can be moved up and be swung to the side for X-ray examinations. The position of the hood and the position of the radiant heater interfere with the access to the patient in the open state.

A thermotherapy device, in which a hood, which can be swung backwards out of the way, can be swung backwards about a pivot axis lying at the head end of the thermotherapy device, is known from WO 2009/073693. By swinging the hood behind the head end of the patient, the radiant heater must be arranged at a considerable height above the reclining surface, which has an effect on the mechanical stability and transportability of the thermotherapy device.

SUMMARY OF THE INVENTION

An object of the present invention is to provide an improved thermotherapy device, which makes possible an operation of the radiant heater both in the closed position and in the open position of the hood.

According to the present invention, provisions are made for the hood to be suspended from the support structure, such that, after moving from the closed position into the open position, it lies with its end facing toward the support structure vertically at least at the height of the radiant heater and horizontally further removed from the support structure than this, such that the hood assumes a position outside of a radiation cone of the radiant heater on the reclining surface. The hood is thus brought to the reclining surface from the ray path of the radiant heater, as a result of which neither a flap in the hood nor IR-transparent materials are needed.

The suspension of the hood from the support structure is preferably embodied, such that, in the open position of the hood, its end facing away from the support structure lies higher than the end facing toward it. Consequently, the accessibility of the reclining surface is improved.

The end of the hood facing toward the support structure is preferably led by means of a coupling mechanism on a circular path about a center of rotation at the fastening of the coupling mechanism to the support structure. The hood can thus be brought by means of a simple, fast movement from the closed position into the open position and vice versa.

The coupling mechanism between the support structure and the hood can preferably be designed as a four-membered gear mechanism with two rocker arms (four-bar linkage). As an alternative, the coupling mechanism between the support structure and the hood can be designed as a redundant five-membered gear mechanism with three rocker arms.

As an alternative, the hood can be pivotably suspended from the support structure by means of a coupling mechanism, which is characterized in that an angular positioning of the hood in relation to the reclining surface associated with the movement of the hood from the closed position into the open position is brought about by means of a chain drive or a positive-locking toothed belt drive coupled to a rocker arm with a chain wheel or toothed belt pulley rigidly connected with the hood and a chain wheel or toothed belt pulley rigidly connected with the support structure. Preferably, a device is then provided for tensioning the chain drive or toothed belt drive.

The support structure is preferably designed as a central column and the coupling mechanism between the support structure and the hood is mounted on the support structure on only one side. On the side opposite the coupling mechanism, operating components, which are installed in the central column (e.g., display and operating unit, emergency respiration unit) are then freely accessible.

One of the rocker arms or the rocker arm can preferably be designed as a housing which is closed on all sides, which encloses the other components of the gear mechanism.

Means are preferably provided for the manual opening and closing of the hood or a drive is provided for opening and closing the hood. For the manual opening, a handle can be arranged on the periphery of the hood on both sides in the area of the hood facing toward the support structure.

As an alternative or in addition, an actuator or a motor, which attaches at the center of rotation between the coupling mechanism and the support structure, is provided for bringing about a rotary movement.

Electrical end position sensors, which detect the open position and closed position of the hood, are preferably present. For example, the end position sensors are designed as sensors, Hall sensors or as light barriers.

In a preferred embodiment, the coupling mechanism is equipped with a spring and/or absorber mechanism.

It is advantageous when the spring and/or absorber mechanism is embodied, such that the hood is moved into the closed position, as long as the hood is swung out of the closed position by less than a threshold value, and it is moved into the fully open position, as soon as the hood is swung out of the closed position by more than the threshold value.

The spring and/or absorber mechanism is preferably integrated into the rocker arm embodied as a housing and is enclosed by same.

The spring and/or absorber mechanism is preferably arranged between at least one rocker arm and the support structure and/or between two rocker arms. In this case, the spring and/or absorber mechanism may have a gas-pressurized spring.

The positioning of the hood can preferably be adjusted via a clamp enclosing a bolt, both in the axial direction of the bolt and in its angular position in relation to the reclining surface.

The present invention is described below on the basis of exemplary embodiments in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
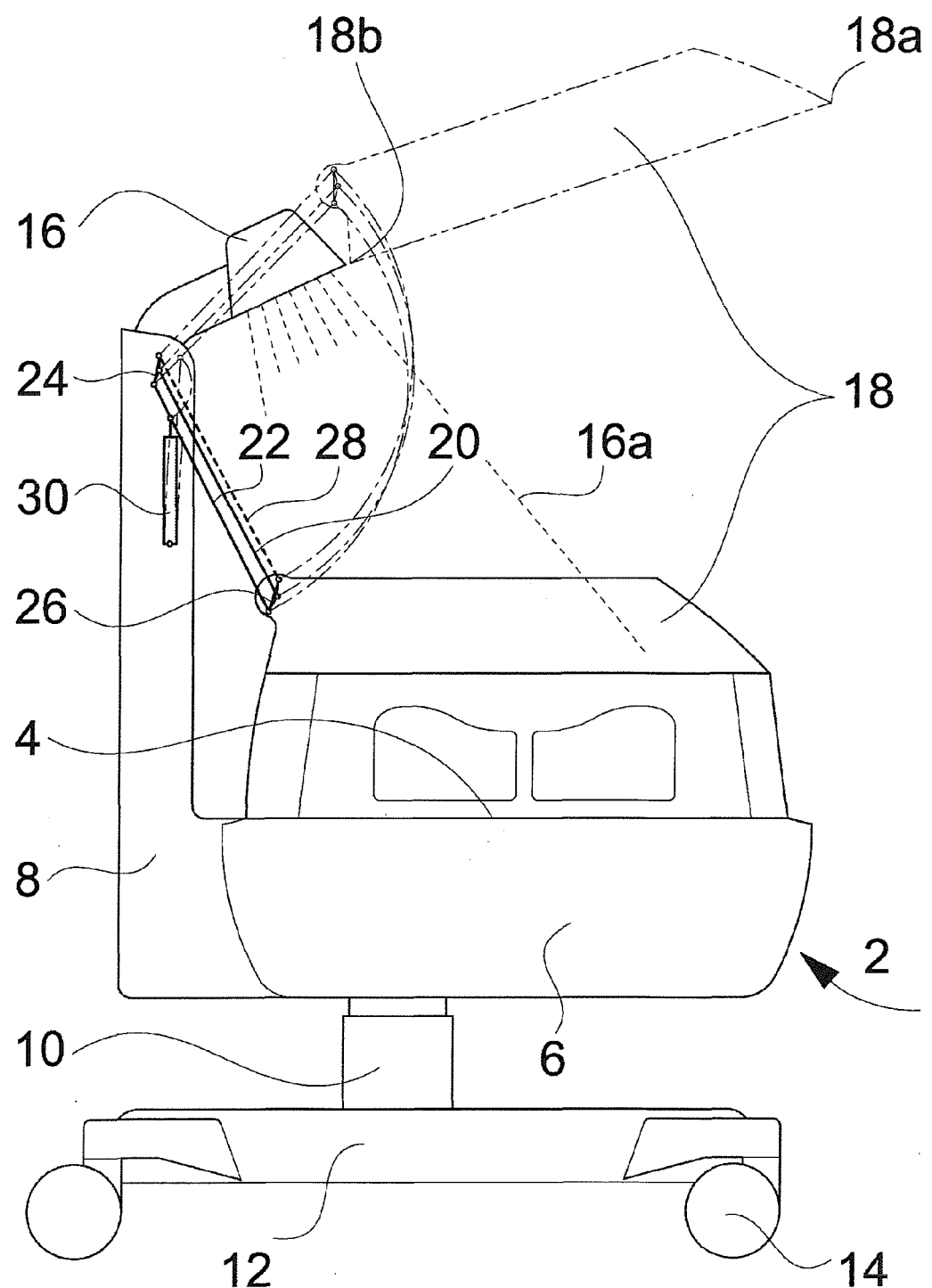
FIG. 1 is a schematic side view of a thermotherapy device with the hood in the closed position in solid lines and the hood in the open position in broken lines.

Referring to the drawings in particular, the thermotherapy device 2 in FIG. 1 has a bordered reclining surface 4, which can receive a newborn lying on the reclining surface. The reclining surface 4 is supported by a horizontal support structure 6, to which a vertical support structure 8 is in turn fastened. The horizontal support structure 6 is connected via a lifting column 10 with a horizontal base 12, which in turn is provided with rollers 14 for the transport of the thermotherapy device.

A radiant heater 16, which is aligned such that a radiation cone, of the radiant heater 16, falls on the bordered reclining surface 4, is suspended at the top from the support structure 8, which is located at the head end of the bordered reclining surface 4. FIG. 1 shows the open position of the hood 18 in broken lines, while the hood 18 in the closed position is shown with solid lines.

The coupling mechanism of the hood 18 to the support structure 8 is embodied here as a four-bar linkage with two rocker arms 20, 22, such that, when swinging from the closed position of the hood 18 shown with solid lines into the open position shown with broken lines, the hood 18 is brought into an oblique position, such that its end 18*a* lying removed from the support structure 8 lies vertically higher than the end 18*b* facing toward the support structure 8. The gear mechanism member 24 is rigidly connected with the support structure 8 and the gear mechanism member 26 is rigidly connected with the hood 18. If the lengths of the gear mechanism members 20 and 22 as well as the lengths of the gear mechanism members 24 and 26 were each identical, then they would form a parallelogram gear mechanism and bring about a simple shifting of the hood 18. Actually, the lengths of the gear mechanism members 20 and 22 or 24 and 26 are all slightly different in the embodiment shown in order to achieve the described oblique position of the hood 18 when opening. This design of the gear mechanism for the hood opening according to the present invention is used to improve the accessibility for the care staff as well as for an X-ray apparatus or the like.

An optional third rocker arm 28 leads theoretically to a static redundancy of the gear mechanism, but is used for stiffening in the practical embodiment, while unfavorable states of the mechanism in the vicinity of dead centers are avoided. The thus expanded gear mechanism can then be designed as a five-membered mechanism instead of as a four-membered mechanism.

The movement of the hood 18 from the closed position into the open position and vice versa can be supported by means of a spring-absorber element 30, for example, a gas-pressurized spring, which, for example, acts between the support structure 8 and the gear mechanism member 22. Instead of this, the spring-absorber mechanism could also act between the support structure 8 and the gear mechanism member 20 or 28 or even between two of the gear mechanism members 20, 22 or 28. In this way, the hood 18 can be moved from the closed position into the open position and vice versa with a movement requiring less force, whereby the spring mechanism is designed, compared with the own weight of the hood 18, such that the hood 18 is automatically pulled into the fully open position when opening, as soon as a predetermined degree of swinging is exceeded, and is closed automatically when closing, as soon as a predetermined degree of swinging is fallen below.

The radiant heater 16 is mounted at the top on the support structure 8 and aligned, such that the hood 18, in its open position, does not hinder the ray path 16a of the radiant heater on the reclining surface 4.

In this way, it is especially possible for the radiant heater 16 to operate during the closed operation, i.e., with the hood 18 closed, in order to thus heat the hood 18, if necessary, in order to prevent condensations on the inner surface of the hood 18. Moreover, it is possible for the radiant heater 16 to be already brought to its operating temperature before the opening of the hood 18, and the hood is then only opened, when the radiant heater 16 can immediately produce the desired heat output on the reclining surface. In the state of the art, in which the radiant heater can be switched on only after opening the hood, a transition time, in which the radiant heater comes to its operating temperature, could pass by, in which the patient is not sufficiently supplied with heat. This problem is overcome by the design according to the present invention, since the radiant heater (16) can be brought to its operating temperature before the hood 18 is open.

Figure 2:
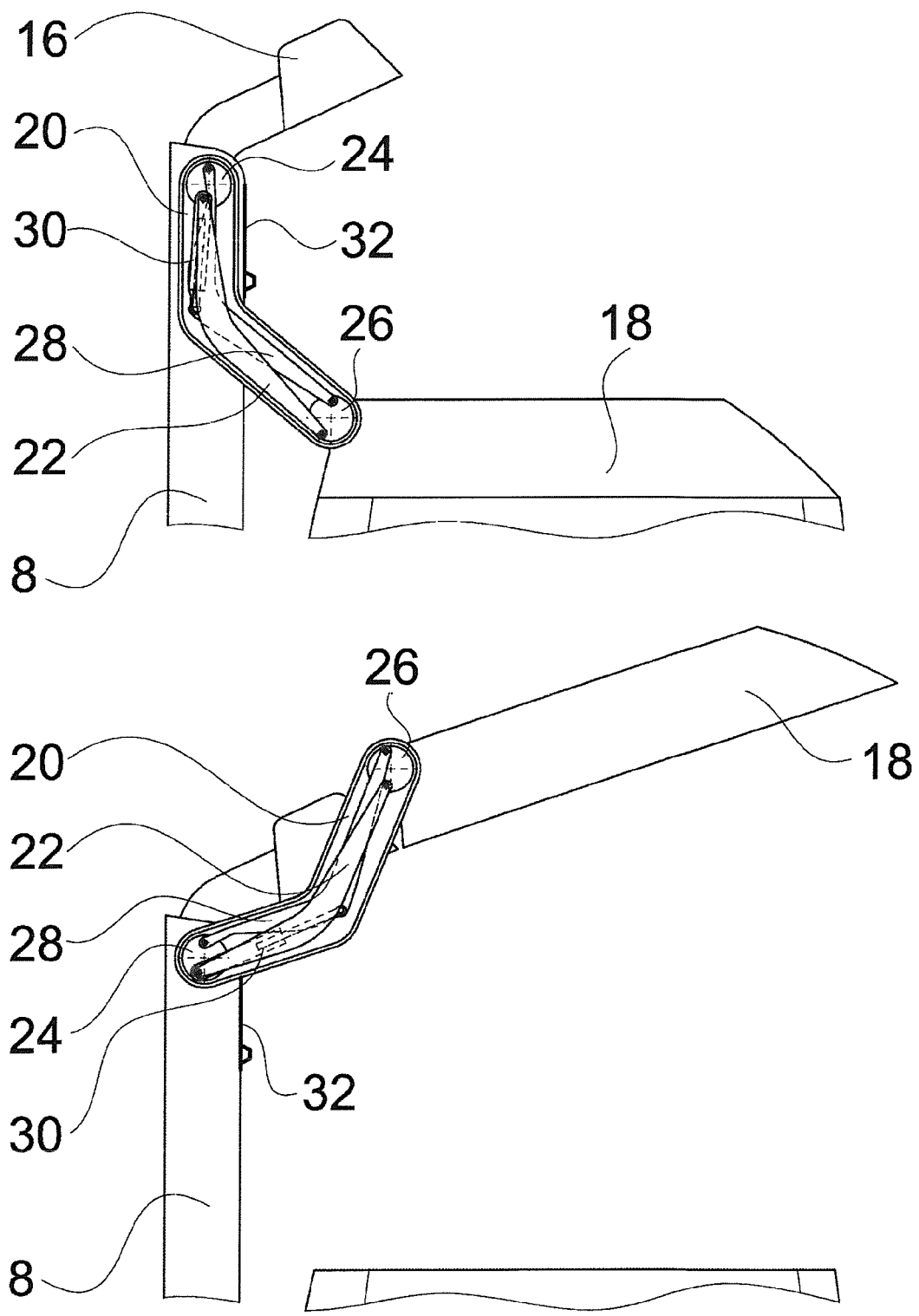
FIG. 2 is partial side views of a thermotherapy device in the closed and open positions, whereby an exemplary embodiment of the coupling mechanism from FIG. 1 is shown.

FIG. 2 shows a partial view of a thermotherapy device with the hood 18 in the closed position (top) and in the open position (bottom), which represents a structural exemplary embodiment of the opening mechanism for the hood 18 described in FIG. 1. The coupling mechanism comprises a first rocker arm 20 designed as a housing (designated as lifting arm below), a second rocker arm 22 and a third rocker arm 28, a connecting link 24 to the support structure 8, a connecting link 26 to the hood 18 as well as a gas-pressurized spring 30, which acts between the connecting link 24 and the rocker arm 28. Both rocker arms 22 and 28 as well as the gas-pressurized spring 30 are installed in the lifting arm 20. The lifting arm 20 as well as the rocker arms 22 and 28 installed in it have an angular shape in the exemplary embodiment, which runs partly parallel to the support structure 8 when the hood is closed. As a result of this, for example, the access to a display and operating unit 32 arranged centrally in the support structure 8 is facilitated.

Figure 3:
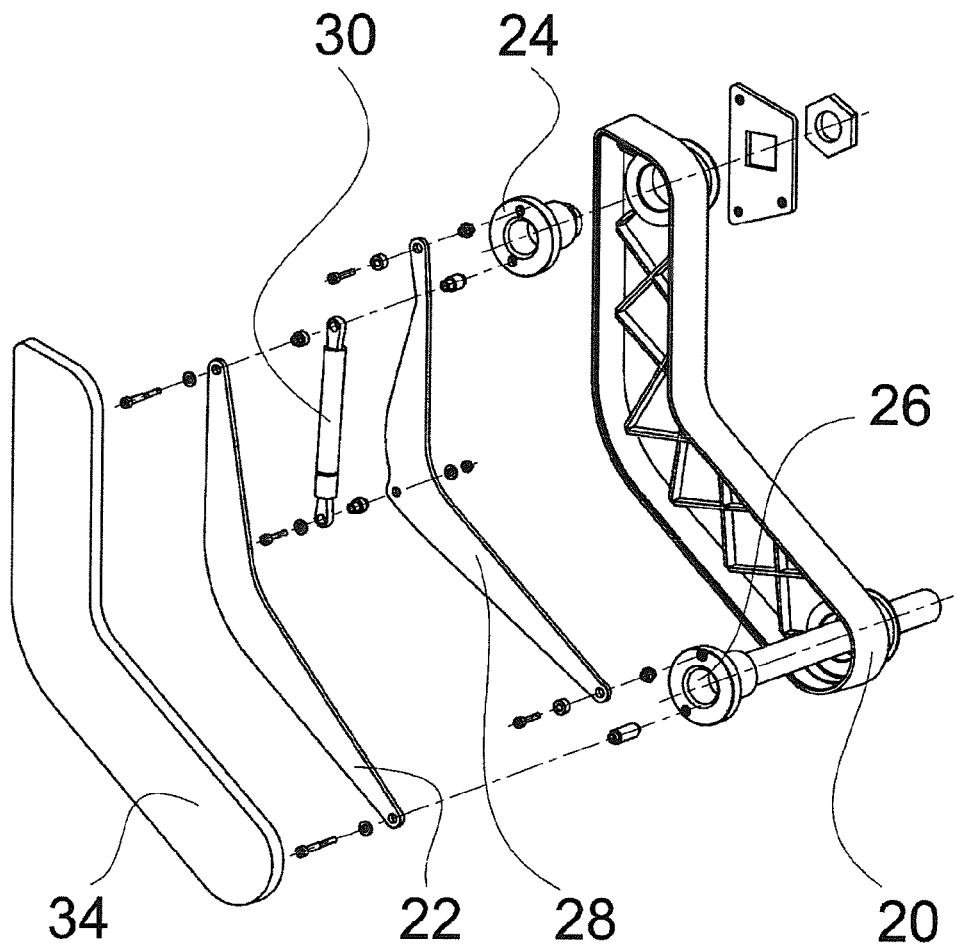
FIG. 3 is an exploded view of the coupling mechanism from FIG. 2.

FIG. 3 shows an exploded view of the above-described exemplary embodiment of the coupling mechanism. The lifting arm is closed with a cover 34, such that the mechanism is completely enclosed, which reduces the risk of injury and facilitates hygiene.

Figure 4:
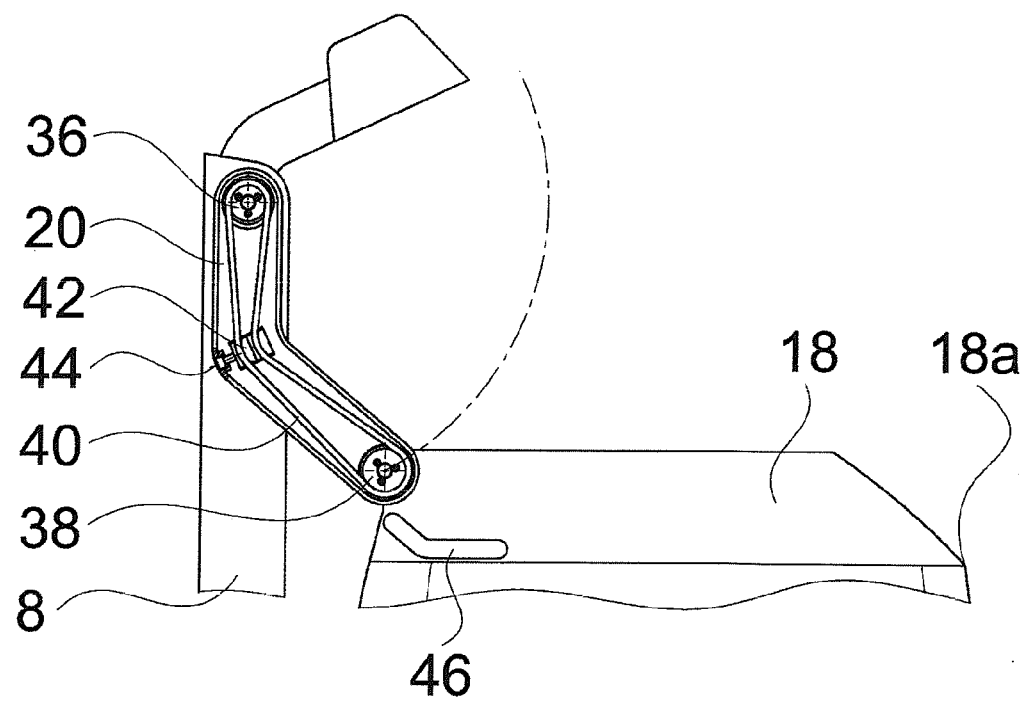
FIG. 4 is a partial side view of a thermotherapy device with a lifting arm with a toothed belt or chain drive.

An alternative embodiment of the coupling mechanism of the hood is shown in FIG. 4. In the lifting arm 20, which is likewise designed as an angular housing, a chain wheel or a toothed belt pulley 36, called first pinion below, is rigidly connected with the support structure 8. The opposite chain wheel or toothed belt pulley 38, called second pinion below, is rigidly connected with the hood 18. A chain or toothed belt 40 is led about the first and second pinions 36, 38 and by means of a deflecting means 42 in order to adapt the mechanism to the shape of the lifting arm 20. The deflecting means 42 may also be used for adjusting the chain prestress or toothed belt prestress, e.g., via a tensioning screw 44. The rigid gear mechanism member, here the lifting arm 20, is coupled to the chain drive or toothed belt drive in such a way that it leads the second pinion 38 and thus the end of the hood 18 facing toward the support structure on a circular path. The chain or toothed belt 40 proceeds via the first pinion 36 and determines the position of the hood 18 in relation to a horizontal plane by means of the angular movement transmitted to the second pinion 38. The second pinion 38 is preferably somewhat larger than the first pinion 36, which, during the opening, brings about an oblique position of the hood 18 in the same desired manner as shown in FIGS. 1 and 2.

In case of a manual operation of the coupling mechanism for the hood 18, a handle 46 is preferably mounted on each side of the hood 18, which is arranged laterally on the end of the hood 18 facing toward the support structure 8. Thus, when swinging the hood 18 open, the operator must not follow the end lying higher than the end position on the side of the hood 18a facing away from the support structure 8. Furthermore, the positioning of the handle at the end of the hood 18 facing toward the support structure also leads to a point of applied force placed favorably in relation to the coupling mechanism. This handle arrangement is just as advantageous in an embodiment of the mechanism according FIGS. 1 through 3.

A support of the manual operation by means of a spring-absorber mechanism, not shown in FIG. 4, as was described above, is also useful in this exemplary embodiment; it can advantageously be arranged between the support structure 8 and the lifting arm 20.

Figure 5:
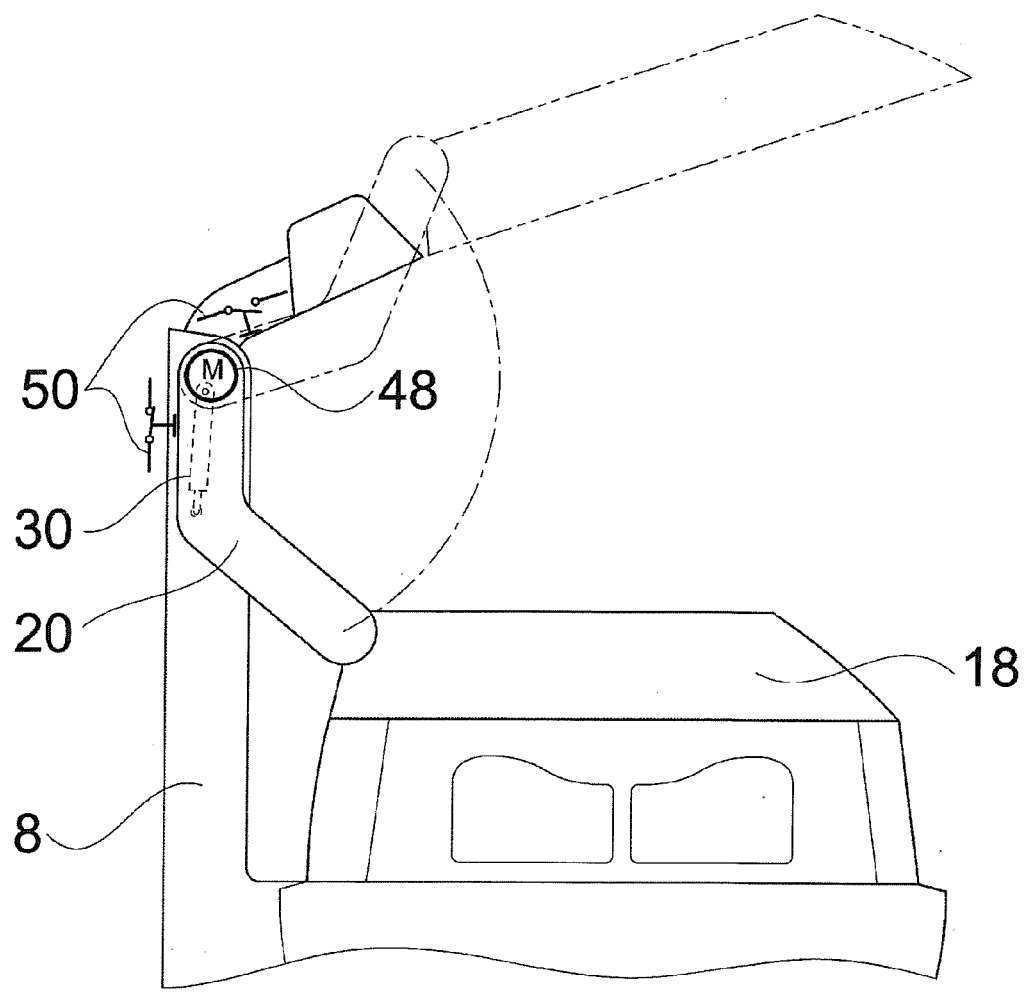
FIG. 5 is a schematic partial side view of a motor drive and electrical sensors for detecting the end positions.

FIG. 5 schematically shows an alternative concept, in which the hood is opened and closed via a motor drive rather than manually. A motor 48 initiates its torque preferably at the center of rotation of the lifting arm 20 connected with the support structure 8. To keep the torque small, the weight of the hood 18 may also be at least partly compensated here, e.g., by means of a spring and/or absorber mechanism, e.g., a gas-pressurized spring 30. In this case, it depends mainly on the spring action, since the velocity of motion can be controlled by controlling the motor.

Both in the motor and the manual drive of the hood opening, the control software of the device must obtain information, in which position the hood is presently located. At least the three states, open, closed and an intermediate position, can be distinguished from one another via two end position sensors 50 designed as sensors in this exemplary embodiment. Instead, or in addition, an angle-measuring means can be provided, which provides more accurate information about the position of the mechanism.

Figure 6:
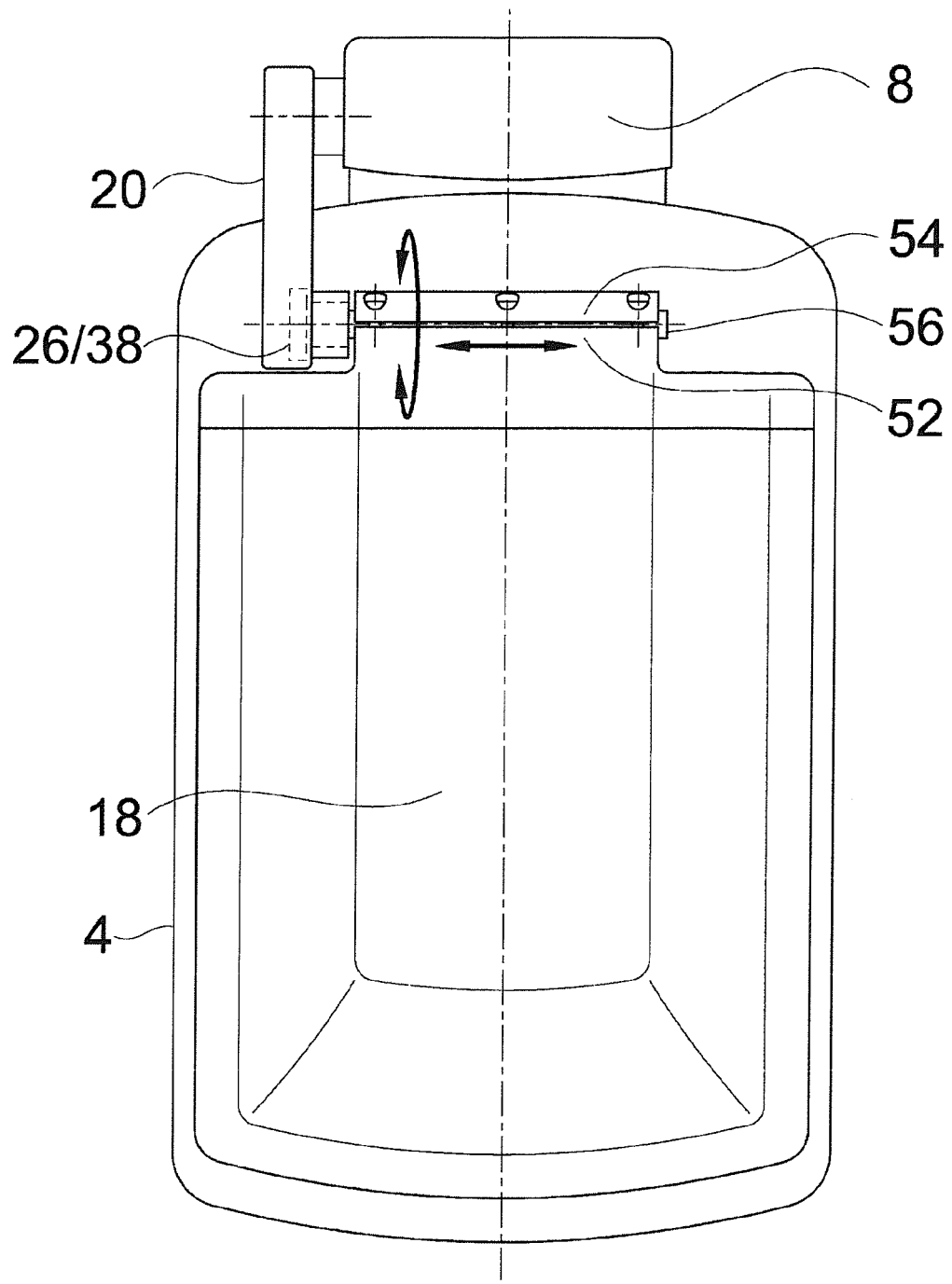
FIG. 6 is a schematic view of a thermotherapy device from above with adjustable hood suspension.

In a preferred embodiment, the hood can be connected with the coupling mechanism via a clamp connection as shown in FIG. 6. A part of a clamp 52 is rigidly integrated into the hood 18, the other part of the clamp 54 is screwed to the first part 52 and locks the bolt 56, which, according to the embodiment, is rigidly connected with the connecting link 26 or the second pinion 38. By means of this mechanism, the hood 18 can be adjusted during assembly both in the transverse direction and in its angular position to the reclining surface 4 in order to thus balance tolerances in the total structure of the device. Thus, the hood 18 can be positioned as accurately as possible to the bordered reclining surface 4 in the closed state, which, for example, is advantageous for sealing between the hood parts. In addition, FIG. 6 shows a preferred arrangement of the coupling mechanism, while the lifting arm 20 is arranged laterally on the centrally arranged support structure 8.

While specific embodiments of the invention have been shown and described in detail to illustrate the application of the principles of the invention, it will be understood that the invention may be embodied otherwise without departing from such principles.

The invention claimed is:

1. A thermotherapy device for the treatment of newborns, the device comprising:
   a bordered reclining surface freely accessible from above for receiving a newborn;

a support structure;

a hood that is movable between a closed position, covering the bordered reclining surface, and an open position, exposing the bordered reclining surface; and a radiant heater suspended from the support structure, to produce a radiation cone directed toward the bordered reclining surface, wherein the hood is suspended from the support structure, such that, after moving from the closed position into the open position, the hood lies with an end of the hood facing towards the support structure vertically at least at the height of the radiant heater and horizontally further removed from the support structure than an end of the radiant heater not facing towards the support structure when the radiant heater is directing the radiation cone toward the bordered reclining surface, such that the hood assumes a position outside of the radiation cone of the radiant heater directed on the reclining surface.

2. A thermotherapy device in accordance with claim 1, wherein the suspension of the hood from the support structure is embodied with a coupling mechanism coupling the hood to the support structure, such that, in the open position of the hood, an end of the hood facing away from the support structure lies higher than the end of the hood facing towards the support structure.

3. A thermotherapy device in accordance with claim 1, wherein the end of the hood facing toward the support structure is led by means of a coupling mechanism on a circular path about a center of rotation on the support structure between the open and closed position;

the closed position of the hood is arranged in the radiation cone of the radiant heater.

4. A thermotherapy device in accordance with claim 3, wherein the coupling mechanism between the support structure and the hood comprises a four-bar linkage as a four-membered gear mechanism with two rocker arms.

5. A thermotherapy device in accordance with claim 3, wherein the coupling mechanism between the support structure and the hood comprises a redundant, five-membered gear mechanism with three rocker arms having an angular shape.

6. A thermotherapy device in accordance with claim 3, wherein the hood is pivotably suspended from the support structure by means of the coupling mechanism, such that an angular positioning of the hood in relation to the reclining surface associated with the movement of the hood from the closed position into the open position is brought about by means of a chain drive or toothed belt drive coupled to a rocker arm with a chain wheel or toothed belt pulley rigidly connected with the hood or a chain wheel or toothed belt pulley rigidly connected with the support structure.

7. A thermotherapy device in accordance with claim 6, further comprising a device for tensioning the chain or toothed belt drive.

8. A thermotherapy device in accordance with claim 3, wherein the support structure is designed as a central column, and the coupling mechanism between the support structure and the hood is mounted on the support structure on one side.

9. A thermotherapy device in accordance with claim 3, wherein:

the coupling mechanism between the support structure and the hood comprises at least one rocker arm; and the rocker arm is designed as a housing closed on all sides, which encloses other components of the coupling mechanism.

10. A thermotherapy device in accordance with claim 3, wherein the coupling mechanism is equipped with a spring mechanism and/or an absorber mechanism.

11. A thermotherapy device in accordance with claim 10, wherein:

the coupling mechanism between the support structure and the hood comprises at least one rocker arm; and the spring and/or absorber mechanism is integrated into the rocker arm which is embodied as a housing and the spring and/or absorber mechanism is enclosed by the housing.

12. A thermotherapy device in accordance with claim 10, wherein:

the coupling mechanism between the support structure and the hood comprises at least one rocker arm; and the spring and/or absorber mechanism is arranged between at least one rocker arm and the support structure and/or between two rocker arms.

13. A thermotherapy device in accordance with claim 10, wherein the spring and/or absorber mechanism is embodied such that the hood is moved back into the closed position, when the hood is swung out of the closed position by less than a threshold value, and the hood is moved into the fully open position, as soon as the hood is swung out of the closed position by more than the threshold value.

14. A thermotherapy device in accordance with claim 3, further comprising an actuator or a motor wherein, for bringing about a rotary movement, the actuator or the motor is provided at the center of rotation between the coupling mechanism and the support structure for opening and closing the hood.

15. A thermotherapy device in accordance with claim 1, wherein the positioning of the hood can be adjusted via a clamp enclosing a bolt both in the transverse direction and in its angular position in relation to the reclining surface.

16. A thermotherapy device in accordance with claim 1, further comprising electrical end position sensors, which detect the open and closed position of the hood.

17. An incubator thermotherapy device comprising:

a bordered reclining surface freely accessible from above for receiving a newborn;

a support structure;

a hood;

a radiant heater suspended from the support structure to provide an output of radiation in the form of a radiation cone directed toward the bordered reclining surface; and a coupling mechanism moveably suspending the hood from the support structure such that the hood is movable between a closed position, covering the bordered reclining surface, and an open position, exposing the bordered reclining surface, such that, after moving from the closed position into the open position, the hood lies with an end of the hood facing towards the support structure vertically at least at a height of the radiant heater and horizontally spaced further from the support structure than an end of the radiant heater not facing towards the support structure when the radiant heater is directing the radiation cone toward the bordered reclining surface, such that the hood assumes a position outside of the radiation cone of the radiant heater directed toward the reclining surface.

18. A thermotherapy device in accordance with claim 17, wherein:

in the open position of the hood, an end of the hood facing away from the support structure is positioned by the coupling mechanism higher than the end of the hood facing towards the support structure; and the end of the hood facing toward the support structure is led by the coupling mechanism on a circular path about a center of rotation on the support structure between the open and closed position, and into and out of the radiation cone.

19. A thermotherapy device in accordance with claim 17 wherein:

the coupling mechanism between the support structure and the hood comprises at least one rocker arm; and the coupling mechanism further comprises a spring mechanism and/or an absorber mechanism integrated into the rocker arm which is embodied as a housing and the spring and/or absorber mechanism is enclosed by the housing or arranged between at least one rocker arm and the support structure and/or between two rocker arms; and the spring and/or absorber mechanism is embodied such that the hood is moved back into the closed position, when the hood is swung out of the closed position by less than a threshold value, and the hood is moved into the fully open position, as soon as the hood is swung out of the closed position by more than the threshold value.

20. A thermotherapy device in accordance with claim 17, further comprising a chain drive or toothed belt drive, wherein the hood is pivotably suspended from the support structure by means of the coupling mechanism, such that an angular positioning of the hood in relation to the reclining surface associated with the movement of the hood from the closed position into the open position is brought about by means of the chain drive or toothed belt drive coupled to the rocker arm with a chain wheel or toothed belt pulley rigidly connected with the hood or a chain wheel or toothed belt pulley rigidly connected with the support structure.

21. A thermotherapy device in accordance with claim 17 wherein:

the radiant heater is mounted on the support structure and is arranged directly above the reclining surface during movement of the hood between the open and closed position, and when the hood is in the open and closed position.

22. An incubator thermotherapy device comprising:

a bordered reclining surface adapted to support a patient;

a support structure connected to said reclining surface;

a hood movably mounted on said support structure between a closed position and an open position, said hood being adapted to cover and enclose said reclining surface and the patient in said closed position;

a radiant heater mounted on said support structure and arranged directly above said reclining surface during movement of said hood between said open and closed position, and when said hood is in said open and closed position, said radiant heater radiating heat in a radiation cone toward said reclining surface;

a coupling mechanism moveably mounting said hood from said support structure between said closed position and said open position, said coupling mechanism arranging all of said hood in said open position further from said reclining surface than said radiant heater is arranged from said reclining surface, said coupling mechanism arranging said hood in said open position further from said support structure than said radiant heater is arranged from said support structure.

23. A thermotherapy device in accordance with claim 22, wherein:

said coupling mechanism arranges said hood in said open position further horizontally from said support structure than said hood is arranged horizontally from said support structure in said closed position.

* * * * *